United States Patent
Creque

(10) Patent No.: US 9,778,149 B2
(45) Date of Patent: Oct. 3, 2017

(54) FLUID SAMPLE SYSTEM AND METHOD

(71) Applicant: Swagelok Company, Solon, OH (US)

(72) Inventor: Andrew J. Creque, Macedonia, OH (US)

(73) Assignee: Swagelok Company, Solon, OH (US)

(*) Notice: Subject to any disclaimer, the term of this patent is extended or adjusted under 35 U.S.C. 154(b) by 96 days.

(21) Appl. No.: 14/700,291

(22) Filed: Apr. 30, 2015

(65) Prior Publication Data

US 2015/0316571 A1 Nov. 5, 2015

Related U.S. Application Data

(60) Provisional application No. 61/987,758, filed on May 2, 2014.

(51) Int. Cl.

| | |
|---|---|
| *G01N 35/10* | (2006.01) |
| *G01F 1/50* | (2006.01) |
| *G05F 3/16* | (2006.01) |
| *G01N 1/22* | (2006.01) |
| *G01N 30/88* | (2006.01) |
| *H02H 9/00* | (2006.01) |
| *H02H 9/02* | (2006.01) |

(Continued)

(52) U.S. Cl.
CPC .............. *G01N 1/2226* (2013.01); *G01F 1/50* (2013.01); *G01N 30/88* (2013.01); *G01N 35/1097* (2013.01); *H02H 9/008* (2013.01); *H02H 9/025* (2013.01); *H02H 9/043* (2013.01); *G01N 2030/324* (2013.01); *G01N 2030/8881* (2013.01)

(58) Field of Classification Search
None
See application file for complete search history.

(56) References Cited

U.S. PATENT DOCUMENTS

| | | | |
|---|---|---|---|
| 3,527,984 A | 9/1970 | Flanagan et al. | |
| 3,527,985 A | 9/1970 | Brown | |
| 3,614,539 A | 10/1971 | Hallenbeck | |

(Continued)

FOREIGN PATENT DOCUMENTS

| | | |
|---|---|---|
| DE | 19607269 | 8/1997 |
| DE | 102007016704 | 10/2008 |

(Continued)

OTHER PUBLICATIONS

International Search Report and Written Opinion from PCT/US15/28403 dated Sep. 17, 2015.

*Primary Examiner* — Daniel S Larkin
(74) *Attorney, Agent, or Firm* — Calfee, Halter & Griswold LLP

(57) ABSTRACT

A fluid sample system includes a control system that operates in the hazardous area and controls one or more valves and optionally receives outputs from one or more transducers and optionally one or more sensors. The fluid sample system includes components that operate in a hazardous area and includes a control system that operates in the hazardous area and that controls one or more electrical devices. The control system communicates across a barrier with a system on a safe side of the barrier with as few as two intrinsically safe couplings including a single pneumatic coupling and a communication link coupling. The control system includes an intrinsically safe voltage boost circuit.

15 Claims, 5 Drawing Sheets

(51) Int. Cl.
H02H 9/04 (2006.01)
*G01N 30/32* (2006.01)

(56) References Cited

U.S. PATENT DOCUMENTS

| | | | |
|---|---|---|---|
| 3,797,311 A * | 3/1974 | Blanchard | G01F 23/265 73/1.73 |
| 3,968,407 A | 7/1976 | Wilson | |
| 4,420,840 A | 12/1983 | Livermore | |
| 4,492,913 A | 1/1985 | Arnold et al. | |
| 4,831,484 A * | 5/1989 | Bruch | H02H 9/02 361/101 |
| 4,967,302 A | 10/1990 | Hutcheon et al. | |
| 5,333,088 A | 7/1994 | Sweet | |
| 5,340,543 A | 8/1994 | Annino et al. | |
| 5,432,711 A | 7/1995 | Jackson et al. | |
| 5,473,647 A | 12/1995 | Eckardt | |
| 5,531,096 A | 7/1996 | Castor | |
| 5,557,084 A | 9/1996 | Myers et al. | |
| 5,583,764 A | 12/1996 | Nail et al. | |
| 5,710,552 A * | 1/1998 | McCoy | G01D 3/08 340/660 |
| 5,712,631 A | 1/1998 | Lewis et al. | |
| 5,741,960 A | 4/1998 | Payne et al. | |
| 5,835,534 A | 11/1998 | Kogure | |
| 5,838,589 A | 11/1998 | Nail et al. | |
| 5,853,027 A | 12/1998 | Winkel et al. | |
| 6,037,857 A | 3/2000 | Behrens et al. | |
| 6,111,738 A | 8/2000 | McGoogan | |
| 6,154,679 A | 11/2000 | Kessler et al. | |
| 6,169,488 B1 | 1/2001 | Ketler | |
| 6,229,448 B1 | 5/2001 | Bennett, Jr. et al. | |
| 6,397,158 B1 | 4/2002 | Bennett, Jr. et al. | |
| 6,397,322 B1 | 5/2002 | Voss | |
| 6,404,609 B1 | 6/2002 | Mansfield et al. | |
| 6,432,265 B1 | 8/2002 | Pursiheimo et al. | |
| 6,469,619 B1 | 10/2002 | Mayercheck et al. | |
| 6,574,652 B2 | 6/2003 | Burkhard | |
| 6,751,520 B2 | 6/2004 | Mathewes et al. | |
| 6,822,431 B2 | 11/2004 | Masuda et al. | |
| 6,889,166 B2 | 5/2005 | Zielinski et al. | |
| 7,152,781 B2 | 12/2006 | O'Dougherty et al. | |
| 7,312,716 B2 | 12/2007 | Kothari et al. | |
| 7,370,791 B2 | 5/2008 | O'Dougherty et al. | |
| 7,390,465 B2 | 6/2008 | Swider | |
| 7,486,495 B1 | 2/2009 | Diederichs et al. | |
| 7,550,943 B2 | 6/2009 | Spartano et al. | |
| 7,651,239 B2 | 1/2010 | Spartano et al. | |
| 7,684,167 B2 | 3/2010 | Burr et al. | |
| 7,723,950 B2 | 5/2010 | Spartano et al. | |
| 7,791,228 B2 * | 9/2010 | Schaefer | H02H 9/008 257/683 |
| 7,843,348 B2 | 11/2010 | Hayford et al. | |
| 7,852,610 B2 | 12/2010 | Uhlenberg et al. | |
| 7,898,786 B2 | 3/2011 | Schmidt | |
| 7,940,508 B2 | 5/2011 | Helfrick et al. | |
| 7,952,321 B2 | 5/2011 | Spartano et al. | |
| 8,014,120 B2 | 9/2011 | Diederichs et al. | |
| 8,059,382 B2 | 11/2011 | Schmidt | |
| 8,081,413 B2 | 12/2011 | Kothari et al. | |
| 8,242,901 B2 | 8/2012 | Indefrey et al. | |
| 8,606,378 B2 | 12/2013 | Zornio et al. | |
| 8,805,308 B2 | 8/2014 | Schubert | |
| 8,885,559 B2 | 11/2014 | Schmidt et al. | |
| 2015/0316571 A1 | 11/2015 | Creque | |

FOREIGN PATENT DOCUMENTS

| | | |
|---|---|---|
| EP | 565217 | 10/1996 |
| EP | 997831 | 5/2000 |
| EP | 883043 | 5/2008 |
| EP | 1503259 | 11/2008 |
| EP | 1883179 | 3/2012 |
| GB | 2398211 | 8/2004 |
| JP | 2005165815 | 6/2005 |
| JP | 2005167058 | 6/2005 |
| WO | 99/56258 | 11/1999 |
| WO | 2006/041949 | 4/2006 |
| WO | 2007/040539 | 4/2007 |
| WO | 2008/048550 | 4/2008 |

\* cited by examiner

P&ID DIAGRAM OF TYPICAL ANALYTICAL FLUID SYSTEM

FLUID SAMPLE SYSTEM AND METHOD

RELATED APPLICATIONS

This application claims the benefit of pending U.S. provisional patent application Ser. No. 61/987,758 filed on May 2, 2014 for FLUID SAMPLE SYSTEM AND METHOD, the entire disclosure of which is fully incorporated herein by reference.

TECHNICAL FIELD OF THE DISCLOSURE

The inventions relate to fluid sample systems, and more particularly to fluid sample systems that operate in hazardous areas.

BACKGROUND OF THE DISCLOSURE

Analytical fluid sample systems are used to prepare and condition a fluid sample stream for analysis as part of a analytical fluid system. A common but not exclusive application is analysis of gas sample streams. The sample streams may be analyzed using a gas chromatograph or other analyzer. Each fluid sample stream is conditioned by the fluid sample system prior to the sample stream being received and processed by the analyzer. In cases where the fluid may be flammable or should be contained, the fluid sample system is physically disposed within a hazardous area that is isolated from the surrounding ambient environment. The ambient environment outside the hazardous area is commonly referred to as a safe area. Between the hazardous area and the safe area is a barrier that physically isolates the safe area from the hazardous area. The barrier may be an electrical barrier that limits power and heat in order to prevent an incendiary condition, and/or a physical barrier such as an explosion proof or pressurized/purged enclosure, as is known.

The fluid sample system conditions the sample streams in the hazardous area by regulating pressure of the sample streams and filtering the sample streams as is known. In addition, the fluid sample system may monitor in the hazardous area various sample stream parameters such as pressure, temperature and flow rate. Various electrical signals are typically produced in the hazardous area that relate to the parametric information from pressure sensors, proximity sensors and temperature sensors. Sensors and actuators such as for valves in the hazardous area must be intrinsically safe (i.e. incapable of igniting flammable vapors), explosion proof or purged/pressurized.

In known analytical fluid systems, the analyzer is disposed in the safe area, meaning that the conditioned fluid sample stream and the parametric signals must cross over the barrier in a safe manner to maintain the integrity of the boundary between the hazardous side and the safe side. Furthermore, a control system that is used to control and/or monitor operation of the fluid sample system, for example various valves and sensors, is fully disposed in the safe area. Thus, the control and output signals also must cross the barrier in a safe manner. Each location of crossing the barrier must be done with a dedicated safe coupling or connection—this includes each parametric electrical signal, each pneumatic signal, each control signal and the fluid sample stream.

SUMMARY OF THE EXEMPLARY EMBODIMENTS

A first inventive concept presented herein provides a fluid sample system that operates in a hazardous area. In an embodiment, the fluid sample system includes a control system that operates in the hazardous area and controls one or more valves and optionally receives outputs from one or more transducers and optionally one or more sensors. Additional embodiments of this concept are presented herein.

A second concept presented herein provides a fluid sample system that operates in a hazardous area and includes a control system that operates in the hazardous area and that controls one or more electrical devices. The control system communicates across a barrier with a system on a safe side of the barrier with as few as three safe couplings including a single pneumatic coupling and a communication link coupling and an electrical power source coupling. Additional embodiments of this concept are presented herein.

A third concept presented herein provides a fluid sample system that operates in a hazardous area and includes a control system that operates in the hazardous area and that controls one or more electrical devices. In an embodiment, the control system includes a voltage boost circuit in the hazardous area, with the voltage boost circuit being intrinsically safe. The voltage boost circuit may be used in other applications other than IS environments. Additional embodiments are disclosed herein.

The various embodiments and concepts disclosed herein further provide in other embodiments a fluid sample system that operates on a hazardous side of a barrier and controls one or more electrical devices, in combination with a fluid sample analyzer and/or other system that operates on the safe side of the barrier.

These and other aspects, advantages and embodiments of the inventions are further described below in view of the accompanying drawings.

DESCRIPTION OF EXEMPLARY EMBODIMENTS

As used herein, the term "intrinsically safe" and derivative forms thereof means an electrical circuit that is restricted in available electrical and/or thermal energy and stored energy, including under fault conditions, so that the circuit is incapable of producing heat or spark or an electric arc that would be sufficient to ignite a hazardous atmosphere. The present disclosure is directed to maintaining an intrinsically safe condition for electrical components and signals on the hazardous side so as to reduce or minimize the number of electrical signals needing to cross the barrier via a safe coupling. The term intrinsically safe as used herein is, therefore, used in the ordinary sense that the term is understood by those skilled in the art.

Figure 1:
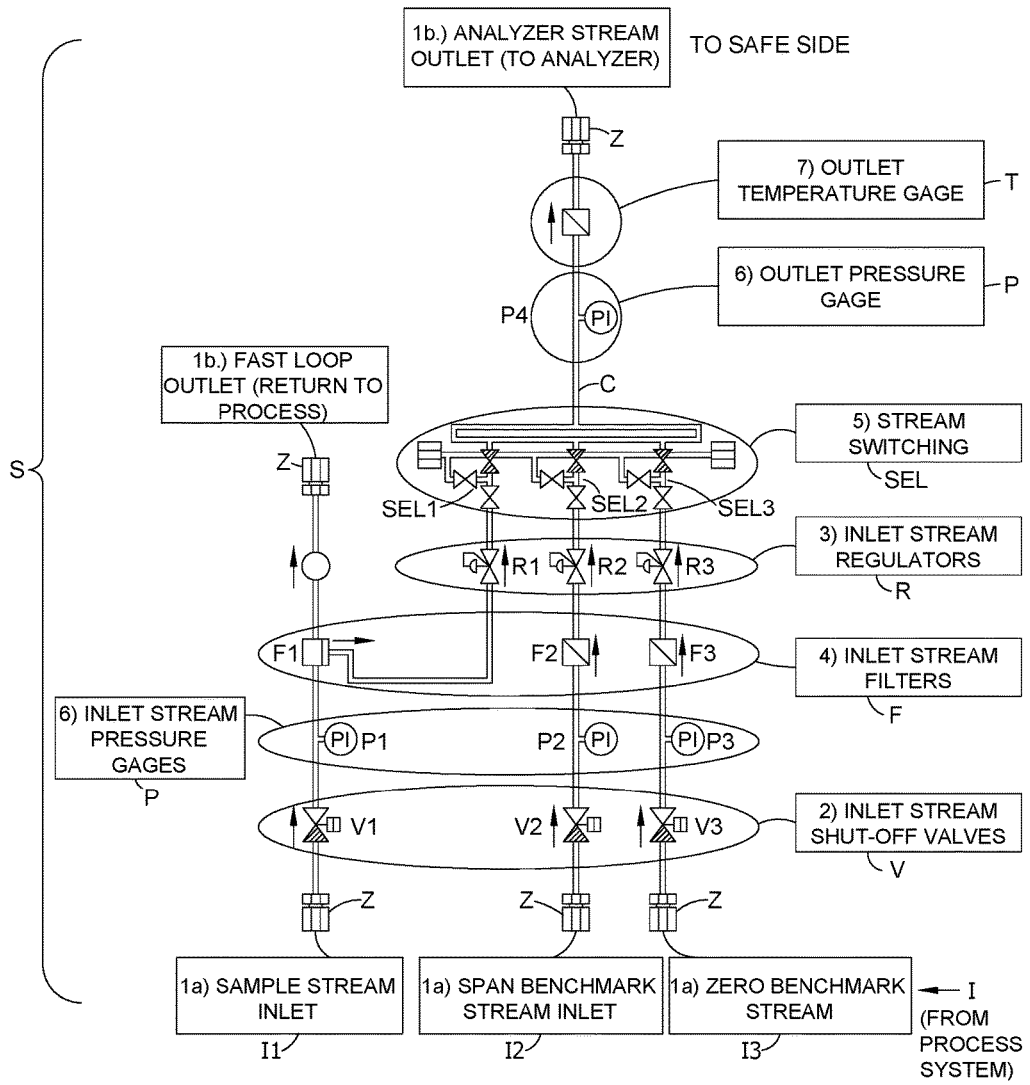
FIG. 1 illustrates an exemplary fluid sample system P&ID diagram.

FIG. 1 is a piping and instrumentation diagram or P&ID of an exemplary but not exclusive type of fluid sample system S (hereinafter the "sample system") that may be implemented to embody the present inventions. The sample system S may include one or more fluid stream inlets I from a process system (not shown), for example, a process sample stream inlet I1, a span benchmark sample stream inlet I2 and a zero benchmark sample stream inlet I3. The span and zero benchmark streams may be used by the fluid sample analyzer (not shown in FIG. 1) for calibration and other operations. Fluid end connectors or fittings Z are provided that connect with a source of each sample stream. A corresponding number of inlet flow control devices, for example, inlet control valves V (for example, shut-off valves) may be used to control flow of the respective inlet sample stream into the sample system S. Accordingly there may be inlet control valves V1, V2 and V3 that respectively control inlet flow of the sample streams I1, I2 and I3. Although the fluid streams I1, I2 and I3 are referred to herein as all being sample streams for convenience, it is recognized that in the example of FIG. 1, the fluid stream I1 is a process sample stream.

A control valve includes an actuator, and for automated systems the actuators may be but need not be in all cases powered electrically, for example, with a solenoid. The term valve is used herein in a shorthand manner to include an associated valve actuator. When an inlet control valve V is open, the associated sample stream I first is filtered through a filter F. Each sample stream I1, I2 and I3 may be filtered by a corresponding filter F1, F2 and F3. Each filtered sample stream is also pressure regulated using a respective pressure regulator R, so that there is a pressure regulator R1, R2 and R3 for each associated sample stream. A stream selector or stream switching function SEL is used to select at any moment in time which if any sample stream I1, I2 or I3 is sent across the barrier (not shown in FIG. 1) for analysis. There is a selector valve SEL1, SEL2 and SEL3 for each associated sample stream I1, I2 and I3. The selector valves SEL1, SEL2 and SEL3 as well as the control valves V1, V2 and V3 may be pneumatically actuated but alternatively may be actuated by other methods as is known.

A selected sample stream from the stream selector SEL passes into an outlet conduit or tube C that has an end connector fitting Z that connects through a safe coupling to a fluid connection (not shown) to the safe side of the barrier and is in fluid communication with a fluid sample analyzer or other system.

In addition to flow control, selection and conditioning, the sample system S may include one or more sensors and devices that detect properties or parameters of the fluid in the sample stream and/or the flow control devices such as the valves SEL and V. For example, just downstream of each inlet control valve V may be a respective pressure transducer P that detects or measures the sample stream pressure. Accordingly there are pressure transducers P1, P2 and P3. Each pressure transducer P outputs an analog electrical signal that is related to the sensed pressure. A fourth pressure transducer P4 may also be provided to measure the pressure of the selected sample stream in the outlet conduit C being sent to the safe side for analysis. A temperature sensor T may be used to detect the temperature of the outlet bound selected sample stream. The temperature sensor T may be but need not be a conventional RTD type sensor that produces an analog signal that is related to temperature of the selected sample stream in the outlet conduit. Alternatively, the temperature sensor T may be incorporated into the pressure transducer P. Temperature readings may be taken at other locations in the sample system S as needed.

Although not shown in FIG. 1, the flow rate of the selected sample stream in the outlet conduit C (or other sample stream elsewhere in the sample system S) may be determined by using two pressure transducers and a controlled or fixed orifice or reducer that forces a pressure drop in the fluid stream across the orifice as is known in the art. A pressure transducer is placed on each side of the fixed orifice so that the differential pressure drop across the orifice can be calculated. By also knowing the upstream pressure, temperature and specific gravity of the fluid stream, the flow rate can be derived by the control system CS in the safe area SA.

Some analytic fluid systems also use a fast loop return to process feature. For example, as shown in FIG. 1, the process sample stream I1 branches from the filter F1 into the pressure regulator R1 and into an end connector Z that provides an outlet from the sample system S to return the sample stream to the process system without analysis on the safe side. This keeps the primary stream as a continuous fast moving stream so that the samples taken and sent to the analyzer are representative of the product, whereas the analyzer stream is a lower flow rate stream.

All of the fluid sample system S components represented in FIG. 1 including the inlet control valves V, the filters F, the regulators R, the stream selector SEL, the pressure transducers P, the temperature sensor T, and the fittings Z are commercially available from Swagelok Company, Solon, Ohio, and therefore will not be described further. A Swagelok pressure transducer is also commercially available that includes a temperature sensor and output. For particular applications and alternative sample system S embodiments, one or more of the various components of FIG. 1 may be optional, and different or additional components may be used as needed.

The arrangement of FIG. 1 is typical in analytical fluid systems which are disposed in a hazardous area, and for manual configurations is monitored by an operator who is physically located inside the hazardous area. The present disclosure provides a system and method for automated control and/or monitoring of the fluid sample system S which increases efficiency and safety. In an automated sample system, the control valves SEL and V may be realized in the form of pneumatically actuated valves. Each control valve uses an associated pilot valve (not shown in FIG. 1) to control delivery of pneumatic pressure to the control valve V. A pilot valve is a solenoid operated valve meaning that electrical energy is needed to operate the pilot valves. The pilot valves may be the only valves in the sample system that use electrical power with all other valves being pneumatically actuated. Electrical energy is also needed to operate the pressure transducers and to obtain the outputs from the temperature sensor. In addition, in an automated system, the operational status of each of the control valves may be monitored, and this monitoring may be done by a proximity sensor PR (not shown in FIG. 1) that is associated with each control valve.

Figure 2:
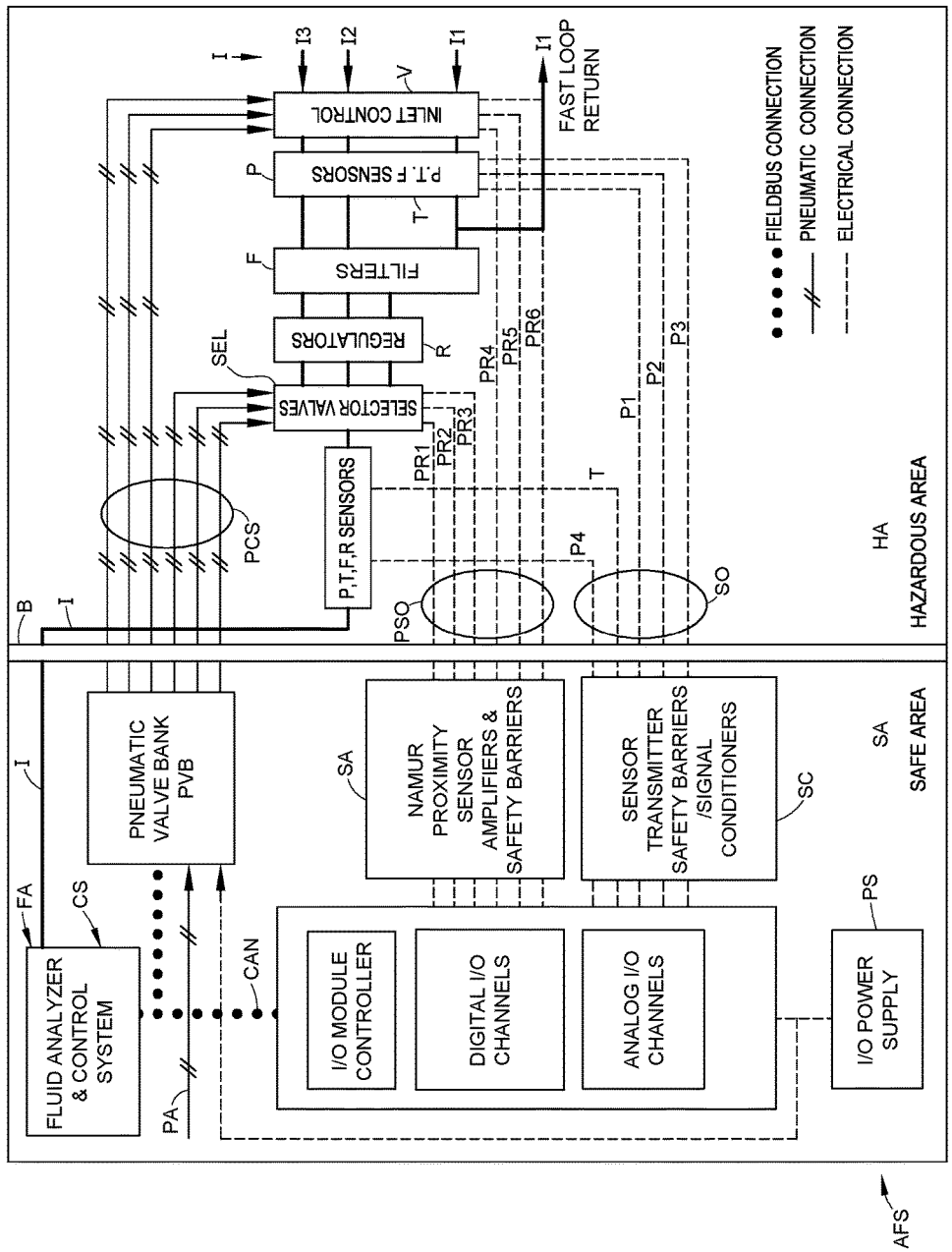
FIG. 2 is a functional block diagram of a prior art automated analytical fluid system.

FIG. 2 illustrates in functional block diagram form an example of a prior art automated analytical fluid system AFS that uses traditional analog I/O across the barrier B. The physical barrier between the safe area SA and the hazardous area HA is represented by the line B. The fluid analyzer FA is located on the safe side, as well as the control system CS that controls operation of the valves and the analog and digital devices that are located on the hazardous side. As is known, some fluid analyzers FA may include the control system CS or portions thereof. Many alternative configurations for the electronics on the safe side are well known. Also, on the safe side is the pilot valve bank PVB that controls delivery of pneumatic pressure to the selector valves SEL and the control valves V on the hazardous side. Each pilot valve PV sends a pneumatic control signal (PCS) across the barrier B. A main supply of pressurized air PA is provided on the safe side to the pilot valves PV (there being six pilot valves corresponding to the number of pneumatically actuated control valves V and SEL), and electrical power is provided to operate the pilot valve control solenoids. Also on the safe side are the digital signal amplifiers SA for the proximity sensor outputs (PSO) from the proximity sensors PR that may be embedded in or otherwise associated with the control valves SEL and V (therefore, there being six proximity sensors PR1 . . . PR6.) Analog signal conditioners SC are also provided on the safe side for the analog sensor outputs SO from the pressure transducers P and the temperature sensors T. The digital I/O and analog I/O circuits have to receive the signals SO and PSO from the transducers and proximity sensors through safety barriers as indicated on FIG. 2. The I/O Power supply PS is also sent across the barrier B to provide power to the pressure transducers P in the hazardous area 14. In order for the control system CS to process the information contained in the outputs SO and PSO, the analog amplifier SC signals are input to an analog I/O of the control system CS, and signal conditioner outputs from the digital amplifiers SA are input to a digital I/O of the control system CS. Each signal requires its own I/O channel and the I/O channels are located on the safe side. Additionally, an I/O power supply PS is provided on the safe side for operating the pilot valves and other components that use electrical energy in the analyzer system. Note further that the sample stream I crosses the barrier into the fluid analyzer FA. The control system CS may communicate with the pilot valve bank PVB and the I/O modules over a conventional field bus, for example, a CAN network.

Automating a fluid sample system S such as in FIG. 2 that is on the hazardous side becomes a challenge because each pneumatic line PCS and each electrical signal line (PSO and SO) that crosses the barrier B must be done through a safe coupling. If the electrical signal lines are connected to explosion proof devices in the hazardous area, the connections must be housed in rigid conduit. If the electrical signals are connected to intrinsically safe devices, the power allowed to enter the hazardous area must be limited to a safe level. With so much of the control being done on the safe side, the system illustrated in FIG. 2 is both complex and expensive.

Figure 3:
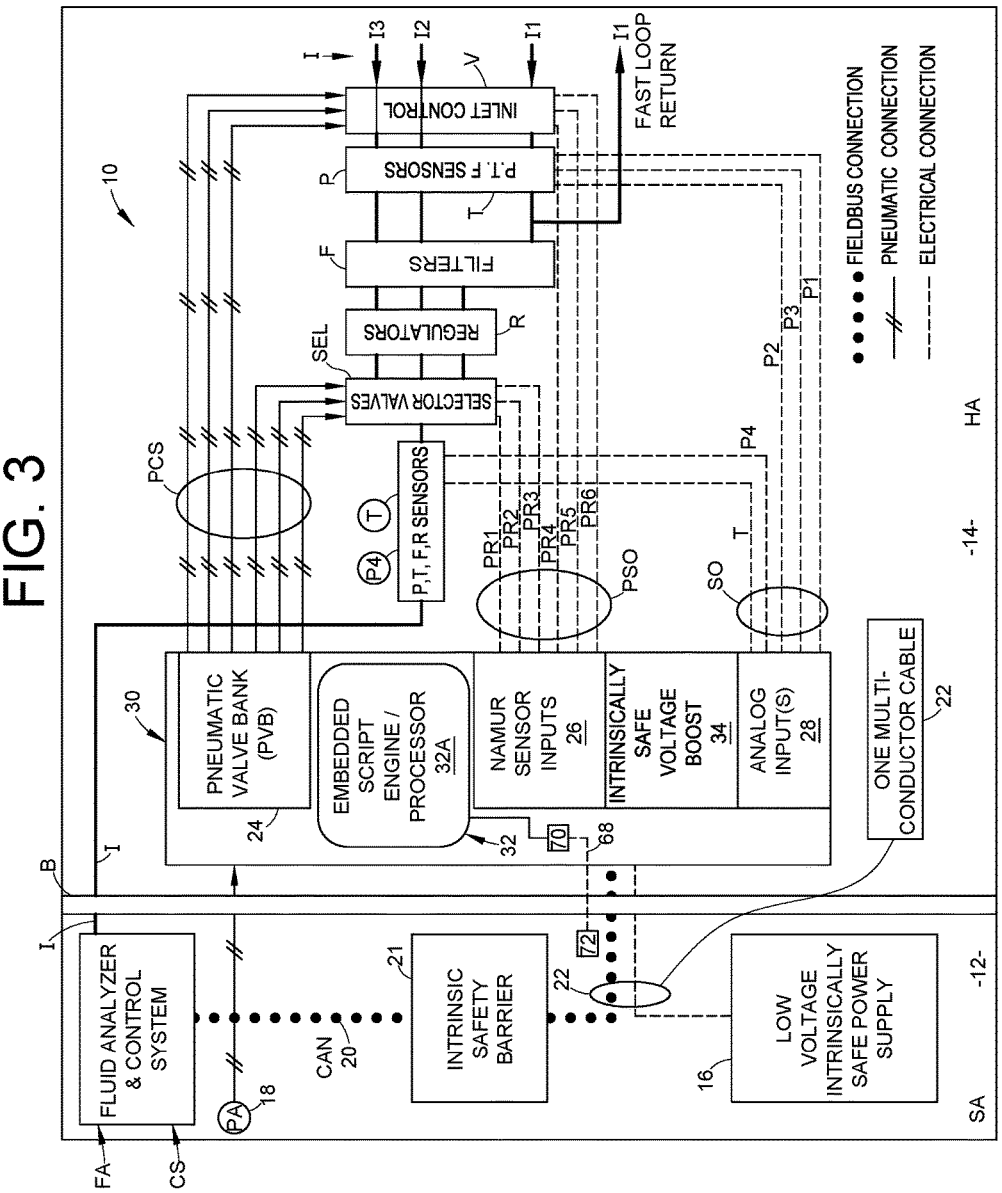
FIG. 3 is a functional block diagram of an embodiment of an automated analytical fluid system in accordance with the teachings herein.

FIG. 3 is an exemplary embodiment of a fluid system 10 in accordance with the teachings and inventive concepts herein, and that may be used, for example, as a fluid sample system, and optionally in combination with a fluid analyzer FA or other system component on the safe side 12 as part of an overall automated analytical fluid system (AAFS.) Those skilled in the art will readily appreciate that the exemplary embodiment may have many different designs and configurations, for example, the many designs that can be used to implement electrical functions and controls. A barrier B separates a safe area or safe side 12 from a hazardous area or hazardous side 14. The hazardous side 14 is designed to be intrinsically safe meaning that the electrical power (as may be defined in terms of heat) used within the hazardous area by various components is below the level required to ignite a potentially explosive atmosphere, even if up to two faults occur within any single component. In FIG. 3, the basic flow control devices and conditioning components may be though need not be the same as described hereinabove, such as the control valves SEL and V, the pilot valves PV, the pressure transducers P, regulators R, filters F, fittings Z, temperature sensors T and proximity sensors PR. Flow control devices other than the valves described herein may also be used for particular applications.

It is noted at this point that although for convenience of understanding and comparison the same P&ID component scheme may be used for the exemplary embodiment of FIG. 3 as was used for FIG. 2, such is not required, and the sample system 10 may be scaled as needed for additional components, sensors, control devices and input streams based on available space in the hazardous area. FIG. 3 is significantly different from FIG. 2, of course, as to the configuration and layout of the components in the safe and hazardous areas, as well as the use of additional circuits that enable FIG. 3 embodiment and alternative embodiments to be realized.

The sample system 10 has much of the control functions moved from the safe side 12 to the hazardous side 14 when compared to FIG. 2, while maintaining an intrinsically safe design. The fluid analyzer FA is on the safe side 12, as well as any related control system CS that sends instructions and processes received information to and from the hazardous area 14. The fluid analyzer FA may be, for example, a common analyzer such as a gas chromatograph, but many other analyzers or other fluid analysis equipment may be used as needed. Also in the safe area is an intrinsically safe (herein, intrinsically safe is also referred to as IS) low voltage power supply 16. The power supply 16 may produce 8.5-12 VDC at 1 amp and be intrinsically safe. An RSA6 series power supply 16 from Pepperl+Fuchs meets these requirements.

A single pneumatic line 18 also crosses the barrier B through a coupling into the hazardous area and is used as the main pneumatic pressure source for operation of the control valves SEL and V. The control system CS may communicate with the control functions on the hazardous side 14 over a conventional two wire CAN network 20. An intrinsically safe barrier 21 may be used to provide IS communication over the CAN network 20 to the hazardous side 14. A multi-conductor cable 22 may be used to provide IS communication between the safe side and the hazardous side as well as to provide the intrinsically safe voltage and current of the power supply 16 into the hazardous area 14. Although a CAN network is preferred for convenience, other network communication designs and protocols may be used as needed.

All other control functions for the sample system 10 may be carried out on the hazardous side 14. This is achieved by moving a pilot valve bank 24 (PVB) to the hazardous side; and providing all digital I/O channels 26 and all analog I/O channels 28 on the hazardous side 14 to receive the signals from the proximity sensors PR and the pressure transducers P and the temperature sensors T, as well as a control system.

As noted above, and in accordance with the teachings herein, an IS sample system control or system manager 30 (also referred to herein as manager 30) is disposed preferably entirely on the hazardous side 14. The manager 30 takes over the control operations of the pilot valves, the control valves and the digital and analog sensor output processing that were previously under the control of the control system CS in the safe area (FIG. 2), and basically operates as a self-contained control system for the sample system 10. The control system CS on the safe side may still be used if needed for particular applications for control of the fluid analyzer FA as well as to interface with the local control manager 30 on the hazardous side, but all local control of the sample system 10 now can be done entirely in the hazardous area in an intrinsically safe manner. In this sense, the control system CS simply provides an interface between the fluid analyzer FA and the sample system 10 that is disposed entirely on the hazardous side. This eliminates almost all need for IS electrical signal transfer across the barrier B because the manager 30 communicates all sample system 10 data and information (and may receive instructions and programming/software updates) with the control system CS over a communication connection that preferably but not necessarily is digital. For example, a digital communication connection may comprise a simple two wire connection that may be realized, for example, with a standard IS CAN connection (further described below herein) or alternatively may be a wireless digital communication connection. Other alternative digital and non-digital communication connections may be used as needed.

The manager 30 may be realized in part with a low power microcontroller 32 such as a 32 bit microprocessor that has on-chip memory and built in CAN interface capability. Moreover, the microcontroller 32 for the manager 30 preferably but not necessarily includes an embedded script engine 32A such as LUA. This embedded script engine 32A allows the manager 30 to be programmed for local control on the hazardous side 14 to control operation of the sample system 10. An example of a suitable microcontroller 32 capable of hosting an embedded script engine 32A is an ARM Cortex M3 processor available from NXP, STM or Atmel; however, many other devices, circuits and software implementations may alternatively be used. The communication between the control system CS on the safe side and the manager 30 on the hazardous side also allows for programming changes and script uploading to the manager 30 from the safe side.

In order to provide local control within the IS hazardous zone 14, an intrinsically safe voltage boost 34 is provided. The IS voltage boost 34 is described in greater detail below. The voltage boost circuit accepts low voltage intrinsically safe power input that is not suitable for powering most sensors, transmitters and valve actuators, and boosts the low voltage input to a suitable level in an intrinsically safe manner. In an embodiment, the voltage boost 34 receives the low voltage 8.5-12 V supply from the IS power supply 16 in the safe area 12 and boosts the voltage up to a nominal 24 V level up to a maximum of 28 V even under fault conditions, on the hazardous side 14. The IS voltage boost 34 may be realized by using current control associated with the voltage boost 34. The voltage boost 34 supplies sufficient voltage so that the manager 30 can manage the control valves and the pressure transducers or any other device on the hazardous side 14 that need more than 12 VDC.

Figure 4:
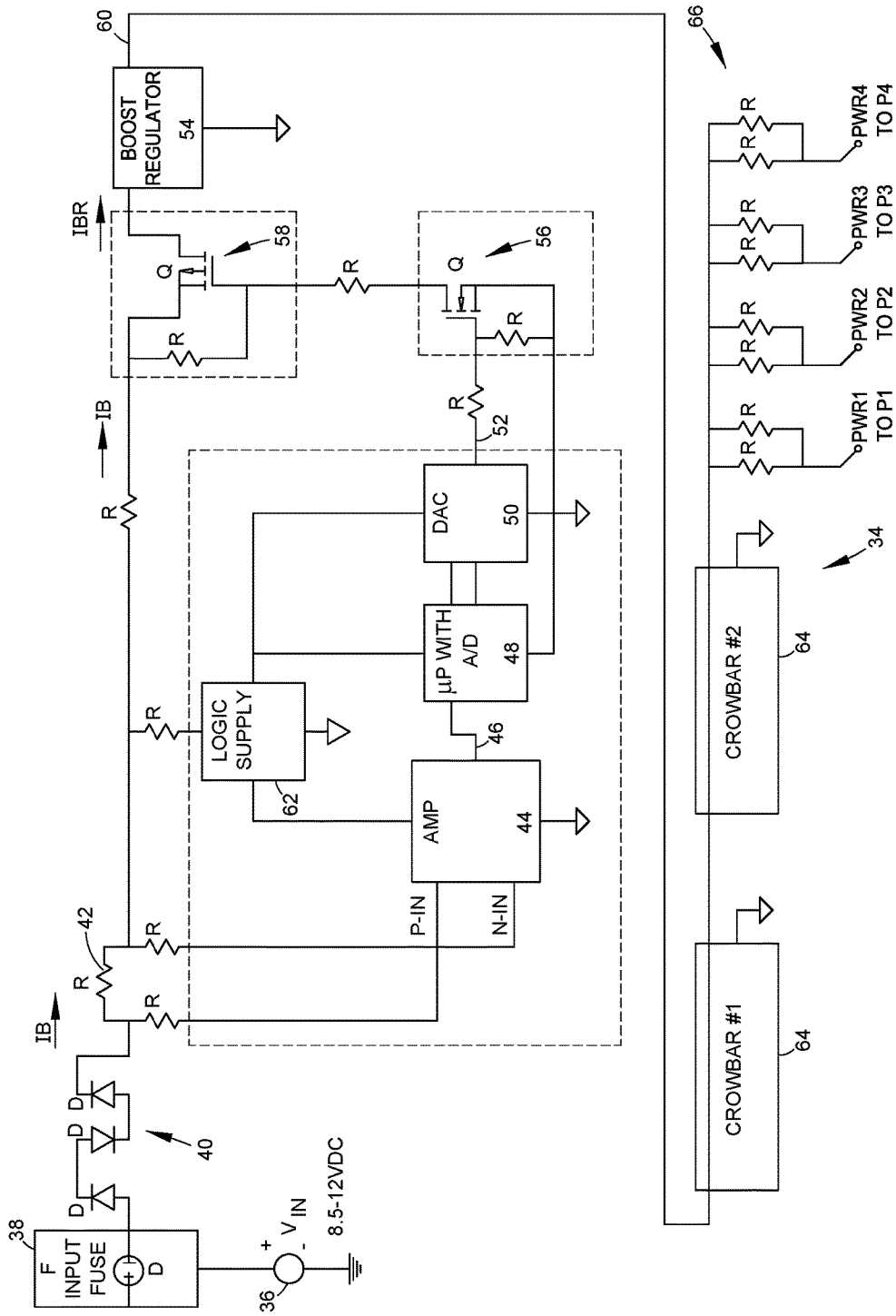
FIG. 4 is a functional block diagram of an embodiment of a voltage boost circuit.

With reference to FIG. 4, an embodiment of the voltage boost 34 is illustrated, however, many different and alternative embodiments may be used as needed. The voltage boost 34 is an intrinsically safe circuit that provides a regulated nominal output voltage of 24 VDC but with current control so as to maintain the power of the circuit within IS requirements. The voltage boost 34 receives input voltage and current from a voltage supply 36 which may be, for example, a 8.5-12 VDC input from the IS voltage supply 16 (FIG. 3) on the safe side 12 of the barrier B. The IS voltage supply 16 may be realized using series RSA6 power supplies available from Pepperl+Fuchs, Germany. The input voltage 36 is connected through a fuse 38 to a series of one or more blocking diodes 40. The blocking diodes 40 are provided to prevent excess current back across the barrier B. The fuse 38 is part of the IS performance for limiting current IB into the voltage boost circuit 34 and prevents the voltage boost 34 from experiencing excessive current flow, which translates into excessive power and temperature rise.

A small current sense resistor 42 is provided in series with the input current IB, which produces a current sense voltage signal that is input to a voltage amplifier 44. An example of an amplifier that may be used is the LT1999 series from Linear Technology Corporation, Milpitas, Calif. The output 46 of the amplifier 44 is input to a microprocessor 48 that includes an analog to digital converter (A/D) to digitize the analog output from the amplifier 44. The microprocessor 48 monitors the input current level IB and manages the level of the current IB that flows through the fuse 38 and that is input to the voltage boost regulator (54.) If the current IB increases so as to make the input power too high, the microprocessor 48 can shutdown the voltage boost 34 before the power levels get unsafe, and also before the fuse 38 breaks. In this regard, the microprocessor 48 along with the amplifier 44 and the DAC (50 described below) act as a fuse current manager CM. An example of a microprocessor 48 is an 8 bit microprocessor with on-chip A/D converter, such as the PIC12F series from Microchip Technology Inc., Chandler, Ariz. An exemplary DAC is the LT2630 series from Linear Technology Corporation; however, many other devices and circuits may be used as needed.

The digital output of the microprocessor 48 which corresponds to the input current IB is input to a digital to analog converter (DAC) 50. The analog output 52 from the DAC 50 is used to regulate and control the current level IBR that is input to a voltage boost regulator 54. The DAC output 52 is used to control the gate voltage on a first transistor 56 such as an FET which in turn controls the gate voltage on a second transistor 58 which may also be an FET. This operation regulates the source/drain current through the second FET 58 which is the current IBR into the voltage boost regulator 54. Exemplary FET devices are a SUM110P P-channel series FET from Vishay, Shelton, Conn., for the second transistor 58; and a Si2300 series N-channel series FET from Vishay for the first transistor 56.

The boost regulator 54 produces in an embodiment a regulated output 60 of 24 VDC from the 8.5-12 VDC supply voltage 36, but with a controlled current and over-voltage protection so as to operate within IS requirements. The voltage boost 34 produces this output voltage for components of the sample system 10 that require higher operating voltage without requiring high current. For example, the pressure transducers P (FIG. 3) may require between 12 and 24 VDC to operate. The voltage boost regulator 54 may be realized in the form of an inductive/capacitive switching boost regulator. The boost regulator 54 may be realized for example with a DC to DC switched mode boost converter which are commercially available; however, other voltage boost regulators may alternatively be used as needed.

The boost voltage of 24 VDC is but one example and other voltage levels may be used as required as determined by the type of device using the supply, such as the control valves, the pressure sensors and so on.

A Zener type voltage regulator 62 may be used to clamp the input voltage 36 to a lower level that may be used as a logic power supply for the amplifier 44, microprocessor 48 and the DAC 50.

The voltage boost regulator 54 output is input to one or more crowbar circuits 64. The crowbar circuits 64 may be conventional in design and operate in effect as high speed low resistance Zener switches that shunt the boost regulator output 60 to ground if the voltage exceeds IS performance. The crowbar circuits 64 are a backup feature in case the fuse current manager operation of the microprocessor 48 circuit response time is not fast enough to protect the system. When the crowbars 64 fire, the resultant current spike will either blow the fuse 38 or will cause the fuse current manager to shutdown the voltage boost 34. The voltage boost output 60 may be used to source supply power to the four pressure transducers P1 . . . P4, for example. Each pressure transducer P receives a respective supply power (PWR1, PWR2, PWR3 and PWR4) through current limiting resistors 66 for IS performance.

Referring back to FIG. 3, the manager 30 may also detect fault conditions or other events that could require attention back on the safe side 12. By having the ability to execute scripts, the manager 30 can monitor various performance aspects of the sample system 10 on the hazardous side 14 and generate an optional alarm output or other indication signal that is sent to the safe side 12. The alarm output 68 may be but need not be realized, for example, in the form of a conventional NAMUR proximity sensor device 70 (the alarm indicator 70) that includes a resistance that can be changed by the microcontroller 32 based on an input condition, thus providing a two state alarm or indicator device 70 (for example, alarm HI or alarm LO.) Note that the alarm indicator 70 does not actually have to perform as a proximity sensor, but rather simply has operational characteristics that allow it to be used as a switchable device under the control of the manager 30. The manager 30 sets the state of the alarm indicator 70 based on monitored conditions in the hazardous area 14. The output 68 of the sensor 70 is separately wired (two conductors) and crosses the barrier B as a hardwired signal. There preferably is no power in the device 70 so it can cross the barrier B in an IS manner, however, alternatively a sensor 70 may provide an electrical signal that is couples across the barrier B by an intrinsically safe connection. A single channel input barrier 72, for example an MTL7741 available from MTL Instruments Group, Luton, UK, includes a relay with contacts that change state as a function of the resistance level of the alarm device 70. The relay contacts thus provide an IS interface between the alarm device 70 and the safe side 12. It will be noted that an alarm signal may alternatively or in addition may be sent over the IS CAN network 21 via the multi-conductor cable 22. But in some cases it may be desirable to have a hardwired alarm signal provided that will operate independent of the operational status of the CAN network 21. The alarm indicator 70 may control an indicator on the safe side 12 such as a lamp or other visible or auditory device so that personnel on the safe side are made aware of the alarm condition.

Figure 5:
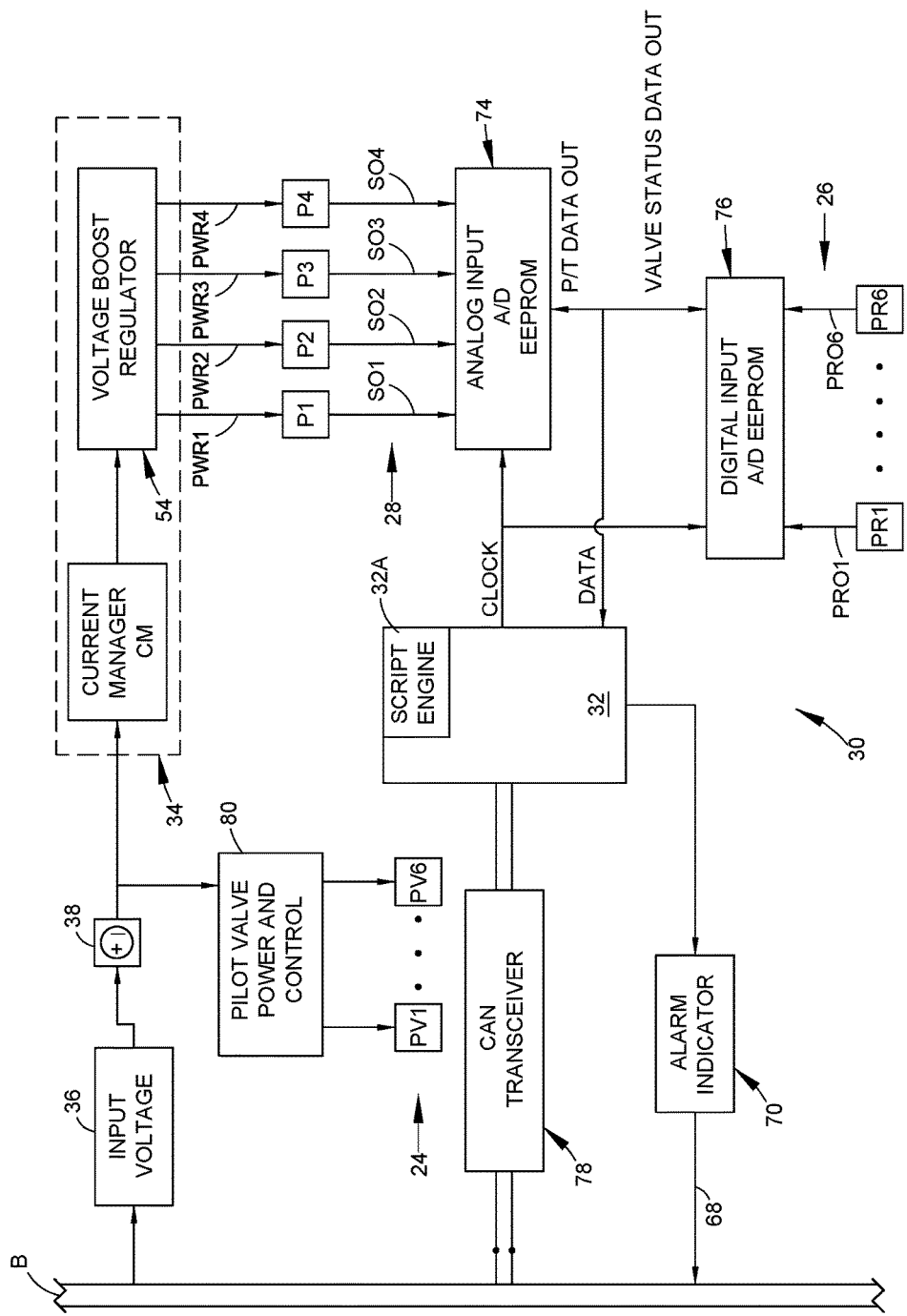
FIG. 5 is a functional schematic of an embodiment of a sample system, such as may be used in the automated analytical fluid system of FIG. 3.

The multi-conductor cable 22 (FIG. 3) in an embodiment may include six conductors for the embodiment of FIGS. 3-5. These conductors in pairs may include: 1) power and ground; 2) the two conductors for the CAN network communication link; and 3) the two conductors for the alarm indicator 70 output 68.

The manager 30 on the hazardous side 14 also may be used to determine flow rate of the various sample streams I, particularly the selected stream that is sent to the analyzer FA. At the outlet conduit C, a second pressure sensor P (not shown) may be used with the outlet pressure sensor P4 and a controlled or fixed orifice to detect the pressure drop across the orifice. The temperature sensor T information along with the differential pressure information across the fixed orifice can be used by the manager 30 to calculate the flow rate of the selected stream going to the safe side 12. In an embodiment, the script engine 32A that is part of the microcontroller 32 may be programmed to perform the needed calculations to determine flow rate, so that the flow rate information can be sent across the CAN communication network 22 along with other information such as pressure, temperature and valve status. In prior systems, each pressure sensor output and the temperature sensor output would all have to be sent across the barrier B with a dedicated IS connection. By having local control logic, for example through the use of scripts with the manager 30, information and be collected and processed on the hazardous side 14 and then the resultant information sent to the safe side 12 via the communication link such as the CAN network.

Although the exemplary embodiment uses a hardwired CAN network or other available communication link across the barrier B, alternative communication methods may be used, including wireless communication.

With reference to FIG. 5, an embodiment of the IS sample system manager 30 of FIG. 3 is illustrated. Although FIG. 5 is primarily illustrating the manager 30, included for convenience and ease of understanding are some of the peripheral devices such as the pilot valves PV and the pressure transducers P and proximity sensors PR that are not physically part of the manager 30 but are part of the overall sample system 10 that is on the hazardous side 14 (FIG. 3.) A low input voltage 36 (from the IS power supply 16 on the safe side 12) is input to the voltage boost 34 (described above with FIG. 4.) The voltage boost circuit 34 may include the fuse current manager CM and the voltage boost regulator 54, both as described above. The boost regulator 54 produces the four output voltages PWR1 . . . PWR4 that are used to power the four pressure transducers P1 . . . P4. An exemplary pressure transducer is a PTX series transducer available from Swagelok Company, Solon, Ohio. Each pressure transducer produces an output voltage (SO1 . . . SO4) for pressure and a second output voltage for temperature, which are connected to the analog input channels 28 (FIG. 3) of an analog input A/D device 74. Alternatively, a pressure transducer may be used that does not include an embedded temperature sensor, so that a discrete temperature sensor may be used as needed, for example, for the selected sample stream temperature sensor T (FIG. 1.) A suitable device is a SITRANS series temperature transmitter from Siemens, combined with a model PR-24-3-100-A-1/4 RTD available from OMEGA Engineering, Inc., Stamford, Conn. The analog input device 74 may be realized, for example, with a commercially available signal conditioning operational amplifier and a multi-channel A/D converter.

Each proximity sensor PR1 . . . PR6 may be embedded in the control valves V and SEL. The control valves V are available as T2A series valves from Swagelok Company, Solon, Ohio; and the selector valves SEL are available as SSV series valves from Swagelok Company. The proximity sensor outputs PRO1 . . . PRO6 are connected to the digital input channels 26 (FIG. 3) of a digital input A/D device 76. The digital input device 76 may be realized, for example, with a multi-channel A/D converter. A suitable proximity sensor for use with the Swagelok valves is a BilEG05-Y1 from Turck.

Both the analog input device 74 and the digital input device 76 may include on-chip addressable EEPROM devices. The microcontroller 32 issues a clock signal 78 to synchronize the microcontroller 32 with the input devices 74/76 because the input devices 74/76 share a common data line into the microcontroller 32. The data line is also used by the microcontroller 32 to address which of the input devices 74/76 will send data to the microcontroller 32 at a given time. The communication between the microcontroller 32 and the peripheral devices may use, for example, an I²C communication protocol. The address information sent by the microcontroller 32 determines at any point in time which input device 74/76 sends data to the microcontroller. The analog input device 74 sends pressure and temperature information and the digital input device 76 sends proximity sensor data which corresponds with valve status.

The microcontroller 32 also communicates with the safe side 12 via a CAN transceiver 78, which may be realized, for example, using a SN65HVD230 series component available from Texas Instruments.

The microcontroller 32 also controls the optional alarm indicator 70 to issue the appropriate alarm HI or alarm LO signal 68 by changing the resistance of the alarm indicator device 70 as described above.

The manager 30 also includes power (80) provided to the pilot valve bank 24. The pilot valves 28 are used to control operation of the control valves V and SEL by delivering pneumatic pressure at selectable times (noting that the six control valves V and SEL as well as the pneumatic connections with the pilot valves 24 are not shown in FIG. 5.) The power for the pilot valves 24 (PV1 ... PV6) may be obtained from a conventional charge pump circuit 80 that receives input power from the 8.5-12 VDC supply 36.

FIG. 3 highlights that simplicity and cost reduction are achieved by having a few as two barriers (not counting the sample stream which has to cross the barrier for analysis.) These two safety barriers may include a first barrier for the single pneumatic line used for system pressure to operate the control valves V and SEL, and an IS barrier for field bus communication signals, for example, the multi-conductor cable 22 and the associated signals thereof.

It is further noted that although the system 10 is described in the exemplary embodiment as a fluid sample system for an automated analytical fluid system, with exemplary application to an IS environment, such is not required. The fluid system 10 may find application beyond fluid sampling applications, and further the fluid system 10 and/or the manager 30 may find application beyond IS environments.

I claim:

1. An automated analytical fluid system, comprising:
    a barrier that separates a safe area from a hazardous area;
    an intrinsically safe fluid sample system that is disposed entirely in said hazardous area, said sample system comprising at least one fluid flow control device and at least one sensor that detects a condition of the fluid; and
    a system manager circuit disposed entirely in said hazardous area, said system manager circuit being configured to control operation of said at least one fluid flow control device and said at least one sensor, wherein one or more of said at least one sensor produces an analog output signal that is received by said system manager circuit;
    said system manager circuit comprising a communication connection to said safe area to communicate information related to said at least one sensor to said safe area.

2. The automated analytical fluid system of claim 1 wherein said communication connection comprises a digital two wire intrinsically safe connection across said barrier.

3. The automated analytical fluid system of claim 1 wherein said communication connection comprises a wireless connection across said barrier.

4. The automated analytical fluid system of claim 1 wherein said system manager circuit is configured to produce an intrinsically safe alarm or indicator signal that is connected across said barrier.

5. The automated analytical fluid system of claim 4 wherein said intrinsically safe alarm or indicator signal is configured to be produced by a switchable device that produces an output that transfers no electrical power across said barrier.

6. The automated analytical fluid system of claim 5 wherein said switchable device comprises a proximity sensor.

7. The automated analytical fluid system of claim 1 wherein said system manager circuit comprises an intrinsically safe voltage boost circuit that is disposed in said hazardous area and that is configured to produce electrical power for said at least one fluid flow control device and said at least one sensor.

8. The automated analytical fluid system of claim 7 wherein said intrinsically safe voltage boost circuit is connectable to receive an intrinsically safe low voltage input of 8.5-12 VDC from a power supply in said safe area.

9. The automated analytical fluid system of claim 8 wherein said intrinsically safe voltage boost circuit comprises a current manager circuit, said current manager circuit comprising a voltage boost regulator circuit, and wherein said current manager circuit comprises a current manager controller that is configured to monitor input current into said voltage boost regulator circuit.

10. The fluid sample system of claim 9 wherein said current manager controller is configured to regulate and control current into said voltage boost regulator by controlling source/drain current through an FET transistor.

11. The fluid sample system of claim 9 wherein said voltage boost circuit and said current manager circuit are intrinsically safe.

12. The fluid sample system of claim 11 wherein said voltage boost circuit and said current manager circuit are intrinsically safe to be disposed in said hazardous area on said hazardous side of said barrier.

13. The automated analytical fluid system of claim 1 wherein said system manager circuit comprises a controller and a script engine.

14. The automated analytical fluid system of claim 13 wherein said system manager circuit is configured to receive instructions and/or software changes for said controller.

15. The automated analytical fluid system of claim 1 wherein said system manager circuit comprises a controller having an embedded script engine.

* * * * *